United States Patent [19]

van Heelsbergen

[11] 4,448,076
[45] May 15, 1984

[54] METHOD AND DEVICE FOR EXAMINATION BY MEANS OF ULTRASONIC BEAMS

[75] Inventor: Teunis R. van Heelsbergen, Eindhoven, Netherlands

[73] Assignee: U.S. Philips Corporation, New York, N.Y.

[21] Appl. No.: 421,557

[22] Filed: Sep. 22, 1982

Related U.S. Application Data

[63] Continuation of Ser. No. 197,366, Oct. 15, 1980, abandoned.

[30] Foreign Application Priority Data

Oct. 15, 1979 [NL] Netherlands .................. 7907595

[51] Int. Cl.³ .................................. G01N 29/04
[52] U.S. Cl. ................................ 73/626; 73/628
[58] Field of Search ............... 73/626, 628, 631; 367/103, 105; 128/660

[56] References Cited

U.S. PATENT DOCUMENTS

| | | | |
|---|---|---|---|
| 3,836,948 | 9/1974 | Burckhardt et al. | 367/105 |
| 4,005,382 | 1/1977 | Beaver | 73/626 |
| 4,070,642 | 1/1978 | Iinuma et al. | 367/105 |
| 4,155,259 | 5/1979 | Engeler | 128/660 |
| 4,164,213 | 8/1979 | Hoelzler | 73/626 |
| 4,180,791 | 12/1979 | Tiemann | 73/626 |
| 4,208,916 | 6/1980 | Thomenius et al. | 73/626 |
| 4,215,584 | 8/1980 | Kuroda et al. | 128/660 |
| 4,224,829 | 9/1980 | Kawabuchi et al. | 73/626 |
| 4,234,940 | 11/1980 | Iinuma | 73/626 |
| 4,241,608 | 12/1980 | Dees | 73/626 |
| 4,241,610 | 12/1980 | Anderson | 73/626 |
| 4,242,912 | 1/1981 | Burckhardt et al. | 73/626 |
| 4,252,026 | 2/1981 | Robinson | 128/660 |
| 4,254,662 | 3/1981 | Kuroda et al. | 128/660 |
| 4,274,148 | 6/1981 | van Thullenaar | 367/105 |

OTHER PUBLICATIONS

Ultrasonic Imaging of Arrays; Macouski; Proceedings of IEEE, vol. 67, No. 4, Apr. 1979.

*Primary Examiner*—Anthony V. Ciarlante
*Attorney, Agent, or Firm*—Jack E. Haken

[57] ABSTRACT

A method of and a device for ultrasonic examination of an object by means of a row of N electroacoustic transducers. Each time a group of M transducers ($M \geq N$) thereof is selected by means of a switching member. These M transducers are first included in transmission networks, transmission signals then being applied to the converters; subsequently, they are included in receive networks, receive signals then being applied to a display device. The transmission and/or receive signals are multiplied by weighting factors between 0 and 1. The sum of the weighting factors during transmission may deviate from that during reception. During transmission and/or reception, at least two different combinations of weighting factors are used, the sum thereof being each time the same. The scanning line density can thus be substantially increased.

9 Claims, 4 Drawing Figures

METHOD AND DEVICE FOR EXAMINATION BY MEANS OF ULTRASONIC BEAMS

This is a continuation of application Ser. No. 197,366, filed Oct. 15, 1980 now abandoned.

The invention relates to a method of examining an object by means of a row of N electroacoustic transducers, comprising the steps of selecting a group of M adjacently arranged transducers (M≧N) for the transmission of an ultrasonic beam and for receiving a part of this beam which is reflected by acoustic discontinuities in the object, and successively applying a transmission signal to at least a part of the group of M transducers and including at least a part of the M transducers in receive networks, the transmission signal intended for each transducer or the receive signal produced by each transducer being multiplied by a weighting factor between 0 and 1. The invention also relates to a device for performing this method, comprising a scanning head with a row of N electroacoustic transducers and a switching member for the selective connection of a group of M adjacently arranged transducers to a transmission device or to a receive device in order to form transmission and/or receive networks, each transmission and/or receive network comprising means for multiplying the passing signals by a weighting factor between 0 and 1.

A method and a device of this kind are known from Netherlands patent application No. 76 12 852 laid open to public inspection. It is also known therefrom that the number of different combinations of transmitted and received ultrasonic beams (scanning lines) should be increased in order to enable more detailed imaging of the object. Because the number of transducers per unit of length of the scanning head cannot be increased indefinitely, other methods are required. One of these methods is described in said patent application. According to this method, alternately even and odd numbers of transducers are activated, so that the transmitted and received beams are shifted each time over half the centre-to-centre distance between two transducers. The number of scanning lines is thus doubled.

It is an object of the invention to achieve a substantial further increase of the number of scanning lines, without making the device essentially more complex.

To this end, the method in accordance with the invention is characterized in that for each group of M transducers the transmission with a given combination of weighting factors is combined with the reception with at least two different combinations of weighting factors or vice versa, the sum of the weighting factors in the different combinations during transmission always being equal to a first value, whilst the sum of the weighting factors in the different combinations during reception always being equal to a second value. The first and the second values may be unequal.

The fact that the weighting factors are between 0 and 1 means that the signal which is least attenuated or most amplified is per definition multiplied by a weighting factor 1. An interrupted transmission or receive network implies a multiplication of the relevant signal by a weighting factor 0.

A further elaboration of the method in accordance with the invention, where the examination time required is substantially reduced, is characterized in that after the transmission of an ultrasonic beam by a group of transducers, reception takes place with at least two different combinations of weighting factors simultaneously.

The device in accordance with the invention is characterized in that there are provided means for realizing, per group of M converters and for one combination of weighting factors in the transmission networks, different combinations of weighting factors in the receive networks or vice versa, the sum of the weighting factors of the different combinations in the transmission networks being equal to a first value, whilst that in the receive networks is equal to a second value, said values may be unequal.

A preferred embodiment of the device in accordance with the invention is characterized in that the weighting factors in the transmission networks are all equal to 1, whilst the weighting factors in the receive networks of the first and the last transducer of the group of M transducers equal a and 1−a, (0≦a≦1), respectively, whilst those in the other receive networks equal 1.

It is to be noted that from German Auslegeschrift No. 26 18 178 a method is also known for substantially increasing the number of scanning lines. According to this method, ultrasonic beams are successively transmitted in a direction perpendicular to the row of transducers and in a number of different directions which enclose a small angle with respect to the former direction. Thus, a fan-shaped beam of scanning lines is formed from each transducer. The information obtained with these scanning lines is displayed on a display screen which is scanned in a pattern of parallel lines. This causes errors in the display. No such errors occur in the method and the device in accordance with the invention because use is made of parallel scanning lines.

The invention will be described in detail hereinafter with reference to the accompanying diagrammatic drawing.

Figure 1:
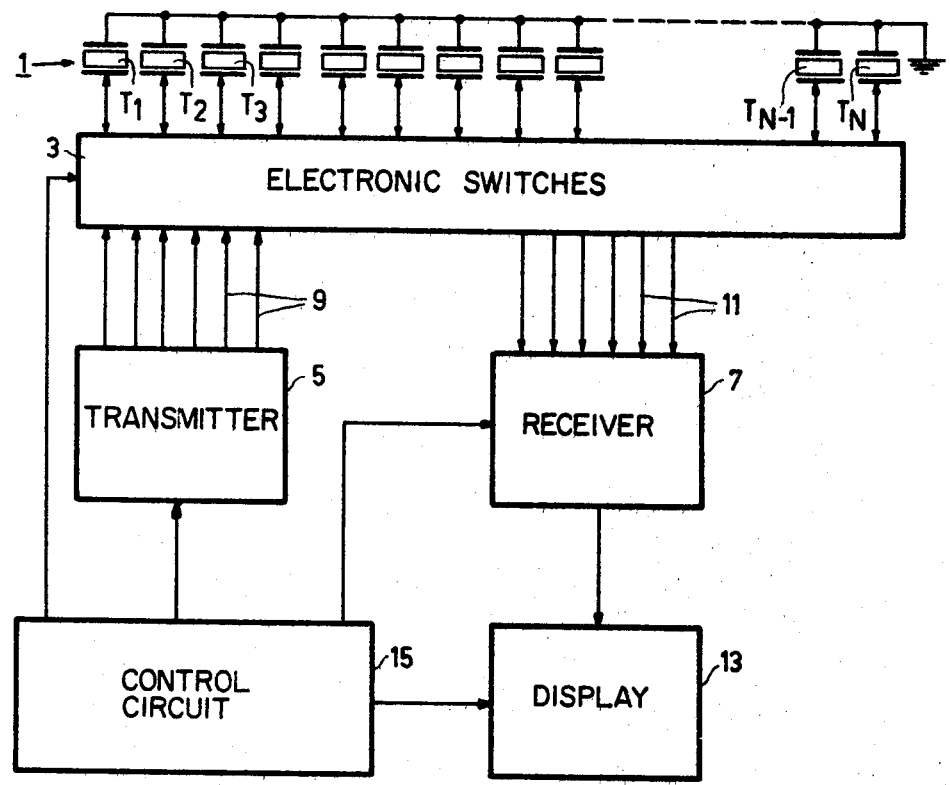
FIG. 1 is a block diagram of an embodiment of a device in accordance with the invention.

The device which is only diagrammatically shown in FIG. 1 comprises a scanning head 1 with a row of N electro-acoustic transducers, $T_1, T_2, \ldots T_N$, for example, of a piezoelectric ceramic material, each transducer comprising two electrodes, one of which is earthed whilst the other is connected to a switching member 3 which comprises N electronic switches for the selective connection of a group of M adjacently arranged transducers to a transmission device 5 or a receive device 7. Therein, M≦N; in the described embodiment, M=6 and six transmission signal lines 9 are present between the transmission device 5 and the switching member 3 and six receive signal lines 11 are present between the switching member and the receive device 7. In conjunction with a transducer and a part of the transmission device 5, each transmission signal line 9 forms a transmission network and, in conjunction with a transducer and a part of the receive device 7, each receive signal line 11 forms a receive network. The receive device 7 is connected to a known display device 13 which comprises a display screen on which an object to be examined is displayed. This display device may also comprise a memory for the temporary storage of the information produced by the receive device 7.

The cooperation between the switching member 3, the transmission device 5, the receive device 7 and the display device 13, required for the formation of an image, is controlled by a principal control circuit 15.

The general construction of the various parts of the device shown in FIG. 1 is known per se (see, for example, Netherlands patent application No. 7608280 laid open to public inspection and German Auslegeschriften Nos. 2618178 and 2628492). Therefore, they will only be elaborated hereinafter in as far as is necessary for a proper understanding of the present invention.

Figure 2:
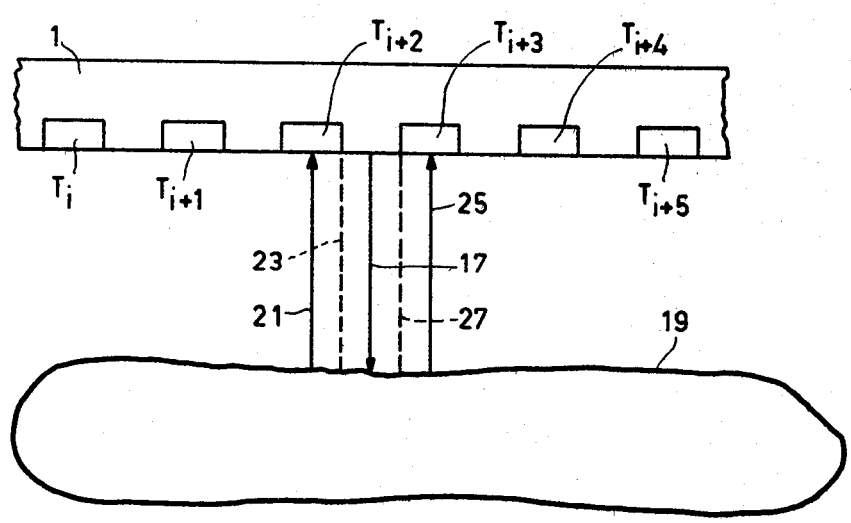
FIG. 2 illustrates an example of the method in accordance with the invention.

An example of the method in accordance with the invention will first be described with reference to FIG. 2. FIG. 2 shows a part of the scanning head 1 with a group of six adjacently arranged transducers $T_i$, $T_{i+1}$, ... $T_{i+5}$ ($1 \leq i \leq N-5$), selected by the switching member 3. Via the transmission signal lines 9, each of these six transducers receives a transmission signal, said six transmission signals all having the same amplitude in this example; in other words, all transmission signals are multiplied by a weighting factor 1 and the number of transducers which effectively contribute to the transmitted ultrasonic beam equals $6 \times 1 = 6$. The transmitted beam is an approximately parallel beam, the axis 17 of which extends perpendicularly to the row of transducers and symmetrically with respect to the selected group of transducers, so halfway between the converters $T_{i+2}$ and $T_{i+3}$.

The transmitted ultrasonic beam is incident on an object 19 to be examined and is partly reflected by acoustic discontinuities in this object. As a result, a reflected beam is formed which is incident on the transducers $T_i$ to $T_{i+5}$ and which generates electrical signals therein which are applied, via the receive signal lines 11, to the receive device 7. The receive networks are adapted so that only the signals are processed which originate from reflected beams whose axes extend parallel to the axis 17 of the transmitted beam. Furthermore, not all weighting factors whereby the receive signals are multiplied are equal to 1, so that not all six transducers contribute equally to the reception. The number of transducers making an effective contribution to the reception, therefore, is smaller than six. FIG. 2 shows some examples where this number equals 5.

In the first example, the weighting factor whereby the signal generated by the transducer $T_{i+5}$ is multiplied equals zero and that whereby the other signals are multiplied equals 1. Only the transducers $T_i$ to $T_{i+4}$, therefore, effectively contribute to the reception, that is to say to the same extent. The axis 21 of the received beam, is therefore symmetrically situated with respect to this subgroup of five transducers i.e. it passes through the centre of the central transducer $T_{i+2}$. The axes 17 and 21 of the transmitted and the received beam, respectively, thus do not coincide, and the scanning line 23 (denoted by a broken line) is situated halfway between these two axes. The scanning line is the symmetry line of the zone scanned by the combination of said transmitted and received beams.

In the second example, the weighting factor whereby the signal generated by the transducer $T_i$ is multiplied equals zero and that whereby the other signals are multiplied equals 1. Therefore, now only the transducers $T_{i+1}$ to $T_{i+5}$ contribute to the reception to the same extent. The axis 25 of the beam received extends through the centre of the central converter $T_{i+3}$ of this subgroup and the scanning line 27 (denoted by a broken line) is situated halfway between this axis and the axis 17 of the transmitted beam.

In the third example, the weighting factor whereby the signals generated by the transducers $T_i$ and $T_{i+5}$ are multiplied equals $\frac{1}{2}$ and that whereby the other signals are multiplied equals 1. The total number of transducers making an effective contribution to the reception, therefore, equals $4 \times 1 + 2 \times \frac{1}{2} = 5$, and the axis of the beam received coincides with the axis 17 of the transmitted beam. The scanning line also coincides with the axis 17.

It appears from the foregoing that one transmitted beam (axis 17) produces three different scanning lines 23, 17, 27. Because the sum of the weighting factors is the same in all three cases, the signals received can be readily compared and further processed in the same manner.

Figure 3:
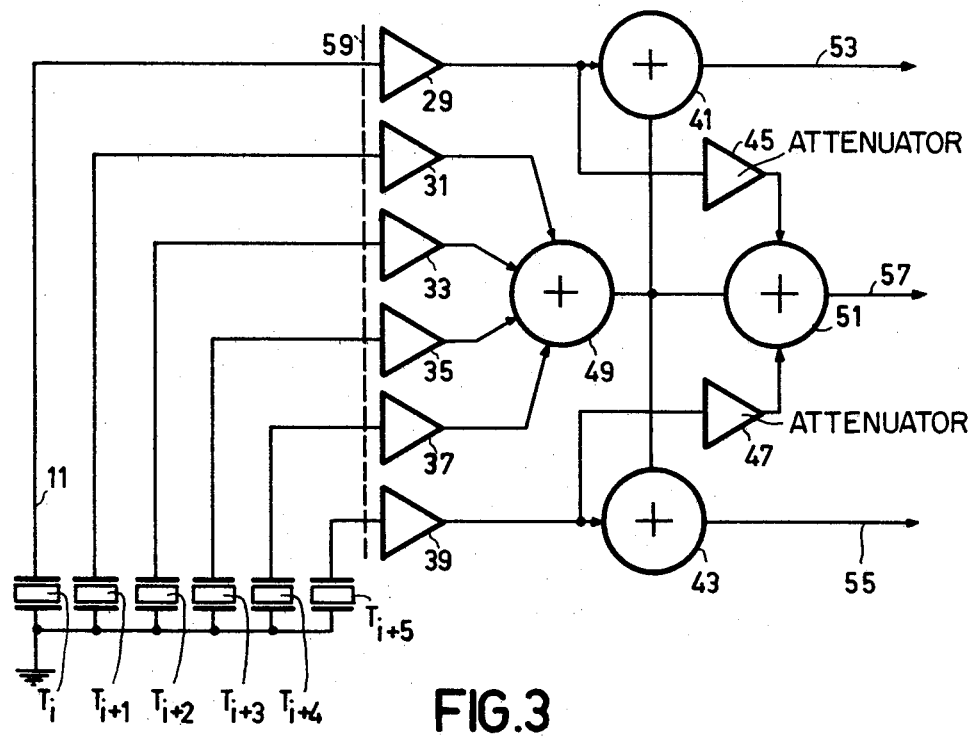
FIG. 3 is a more detailed block diagram of a part of the device shown in FIG. 1.

Obviously, it is possible to transmit a beam with the axis 17 three times in succession and to receive successively beams with the axes 21, 17 and 25. However, the scanning operation is substantially faster when, after a transmitted beam having the axis 17, the three beams with the axes 21, 17 and 25 are simultaneously received and processed, the information being temporarily stored, if desired, in the memory of the display device 13. As will be explained hereinafter, this can be realized in a suitable embodiment of the device in accordance with the invention. To this end, FIG. 3 shows a block diagram of an embodiment of the input section of the receive device 7. For the simplicity of the Figure, the receive signal lines 11 are shown to be directly connected to six transducers $T_i$, ... $T_{i+5}$ with omission of the actually present switching member 3. Each of the receive signal lines 11 is connected to a preamplifier. These preamplifiers are denoted by the reference numerals 29, 31, 33, 35, 37 and 39. The preamplifiers 29 and 39, receiving the signals originating from the extreme transducers $T_i$ and $T_{i+5}$, respectively, are each connected to an adder 41, 43, respectively, and to an attenuator 45, 47, respectively. The other amplifiers 31, 33, 35, and 37 are connected to a common adder 49, the output of which is connected on the one side to the two former adders 41 and 43, and on the other side to a further adder 51 which is also connected to the outputs of the two attenuators 45 and 47.

The described circuit forms a network of three series of six reveive networks, each series of receive networks processing the signals originating from the six transducers. The first series of receive networks terminates in the adder 41 and applied an output signal to the first output line 53, the second series terminating in the adder 43 and applying an output signal to the output line 55, whilst the third series terminates in the adder 51 and applies an output signal to the output line 57. The receive networks in the first series multiply each of the signals of the transducers $T_i$ to $T_{i+4}$ by a weighting factor 1, and those of the transducer $T_{i+5}$ by a weighting factor 0, because the preamplifier 39 is not connected to the adder 41. Analogously, the receive networks in the second series multiply the signals of the transducers $T_{i+1}$ to $T_{i+5}$ by a weighting factor 1 and those of the transducer $T_i$ by a weighting factor 0. The receive networks of the third series multiply the signals of the transducers $T_{i+1}$ to $T_{i+4}$ by a weighting factor 1 and those of the transducers $T_i$ and $T_{i+5}$ by a weighting factor $\frac{1}{2}$.

Therefore, in all cases the sum of the weighting factor equals 5. The output signals simultaneously appearing on the three output lines 53, 55 and 57 correspond to the three beams, having the axis 21, 25 and 17, respectively, described with reference to FIG. 2.

In the described embodiment, the weighting factors of the two attenuators 45 and 47 are constant and equal to ½. It is alternatively possible for these weighting factors to be variable, their sum always being equal to 1. The weighting factors are then a and 1−a, respectively, it being possible to vary a between 0 and 1 by means of a control member (not shown). If this variation takes place continuously, the axis of the received beam can be continuously displaced from the axis 21 to the axis 25 (FIG. 2). The number of scanning lines is then unlimited. The adders 41 and 43 and the associated output lines 53 and 55 can then be dispensed with.

For the embodiments described thus far it has been assumed that the transmitted and received ultrasonic beams have flat wave fronts parallel to the row of transducers. However, it is known to use beams with curved wave fronts for transmission as well as reception in order to focus the beams onto a selected area. This can be achieved, for example, as described in detail in U.S. Pat. No. 3,919,683, by the selective delay of the electrical signals applied to the transducers (during transmission) or produced by the transducers (during reception). To this end, variable delay members must be included in the transmission and/or receive networks. These members may be inserted in the circuit shown in FIG. 3, for example, in front of the preamplifiers 29 to 39 in the receive signal line 11 by interrupting these receive signals lines at the area of the broken line 59.

Figure 4:
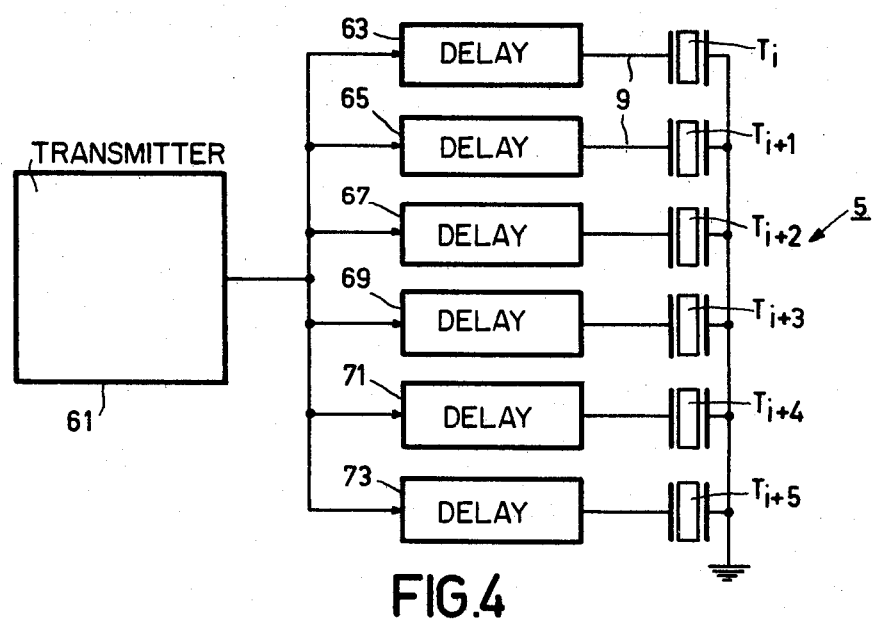
FIG. 4 is a more detailed block diagram of a further part of the device shown in FIG. 1.

FIG. 4 diagrammatically shows an embodiment of the transmission device 5 in which a switching member 3 between the transmission signal lines 9 and the transducers $T_i \ldots T_{i+5}$ has been omitted for the sake of simplicity. The transmission device comprises a transmission signal generator 61, the output of which is connected to six delay elements 63, 65, 67, 69, 71 and 73. Each of these delay elements is connected to one of the six transmission signal lines 9. When the delay elements are suitably adjusted by the principal control circuit 15, the transducers $T_i$ to $T_{i+5}$ transmit a focussed ultrasonic beam.

For the embodiments described above, it has always been assumed that a transmitted beam (axis 17, FIG. 2) is combined with more than one received beam (axes 21, 17, 25). Obviously, it is alternatively possible to combine more than one transmitted beam with one or more received beams. For example, by suitable control of the switching member 3, first the transducers $T_i$ to $T_{i+4}$ and subsequently the transducers $T_{i+4}$ to $T_{i+5}$ can be connected to the transmission device 5, whilst reception takes place by means of the transducers $T_i$ to $T_{i+5}$. Thus, transmission first takes place with the weighting factors 1, 1, 1, 1, 1, 0 and subsequently with the weighting factors, 0, 1, 1, 1, 1, 1.

In the case of transmission or reception with focussed beams, the axis of the beams enclose an angle other than 90° with respect to the row of transducers when the distribution of the weighting factors is not symmetrical with respect to the centre of the group of M transducers. Therefore, the control of the delay elements must be adapted to the distribution of the weighting factors. For example, when the transmission device shown in FIG. 4 applies transmission signals with the same weighting factor to all transducers $T_i$ to $T_{i+5}$, the axis of the emitted beam passes centrally between the transducers $T_{i+2}$ and $T_{i+3}$ and the delay times of the delay elements 67 and 69 must be mutually equal, like those of the delay elements 65 and 71 and those of the delay elements 63 and 73. However, when the signal to the first transducer is multiplied by a weighting factor 0 and the signals to the other transducers are multiplied by a weighting factor 1, the axis of the transmitted beam extends through the centre of the converter $T_{i+3}$ and for the focussing the delay elements 67 and 71 must have the same delay time as the delay elements 65 and 73. The delay element 69 then has its own delay time.

It will be clear that the embodiments described above can be further supplemented. For example, the number M which indicates the number of transducers of the selected group may be other than six. Moreover, more complex distributions of the weighting factors over the M transducers can be used for transmission as well as for reception. The method in accordance with the invention is also particularly suitable for the display at an enlarged scale of a part of an original image with the same line density.

What is claimed is:

1. A method of examining an object with ultrasound energy utilizing a row of N electroacoustic transducers, comprising the steps of:

selecting a group of M adjacent transducers in the row, M being less than or equal to N;

applying first electrical signals to at least part of the group of transducers, the signal applied to each of the transducers being multiplied by a respective one of a first set of amplitude weighting factors, to transmit ultrasound energy as a beam which does not diverge between the group and the object;

receiving said ultrasound energy, which is reflected from the object, with said group of transducers to produce second electrical signals;

applying the second signals to receive networks which multiply each of the second signals by a respective one of a second set of amplitude weighting factors; and applying the second signals to receive networks which multiply each of the second signals by a respective one of a third set of amplitude weighting factors;

wherein the second and third sets of weighting factors are different from each other and the sum of the weighting factors in the second set is equal to the sum of the weighting factors in the third set.

2. A method of examining an object with ultrasound energy utilizing a row of N electroacoustic transducers, comprising the steps of:

selecting a group of M adjacent transducers in the row, M being less than or equal to N;

initially applying first electrical signals to at least part of the group of transducers, the signal applied to each of the transducers being multiplied by an associated one of a first set of amplitude weighting facts, to transmit a first beam of ultrasound energy to the object;

subsequently applying fourth electrical signals to at least a part of the group of transducers, the signal applied to each of the transducers being multiplied by an associated one of a fourth set of amplitude weighting factors, to transmit a second beam of ultrasound energy to the object; and receiving ultrasound energy in the beams which is reflected from the object with the group of transducers to produce second electrical signals;

wherein the first and fourth sets of weighting factors are different from each other and the sum of the weighting factors in the first set is equal to the sum of the weighting factors in the fourth set.

3. The method of claim 1 or 2 wherein the second signals are applied to receive networks which simultaneously multiply the signals by two different sets of amplitude weighting factors.

4. A device for examining an object with ultrasound energy comprising:

a row of N electroacoustic transducers which function to convert electrical transmission signals applied thereto into a beam of ultrasound energy which does not diverge between the transducers and the object and is directed toward the object and to convert ultrasound energy in the beam which is reflected by and received from the object into electrical receive signals;

an ultrasound transmitter for producing electrical transmission signals;

an ultrasound receiver for displaying electrical receive signals;

transmission network means for multiplying the transmission signals produced by the ultrasound transmitter by a first set of amplitude weighting factors;

receive network means for multiplying the receive signals by a second set of amplitude weighting factors and by a third set of amplitude weighting factors and for applying the sets of multiplied receive signals to the ultrasound receiver; and switching means for selectively connecting a group of M adjacent transducers in said row, M being less than or equal to N, to said transmission network means and to the receive network means so that a transmission signal multiplied by an associated one of the weighting factors in the first set is applied to each of the transducers in the group and so that the receive signal from each of the transducers in the group is multiplied by an associated one of the weighting factors in both the second set and the third set of weighting factors;

wherein the second set of weighting factors and the third set of weighting factors are different from each other and wherein the sum of the weighting factors in the second set is equal to the sum of the weighting factors in the third set.

5. The device of claim 8 wherein the group of transducers comprises a row having a first transducer, at least one intermediate transducer, and a last transducer; wherein all of the weighting factors in the first set are equal to 1, wherein the weighting factors in the second set associated with the intermediate transducers are equal to 1, and wherein the weighting factor in the second set associated with the first transducer is equal to a, a being greater than or equal to 0 and less than or equal to 1, and the weighting factor in the second set associated with the last transducer is equal to (1−a).

6. The device of claim 4 or 5 wherein the receive network means simultaneously multiply the receive signals by two different sets of amplitude weighting factors.

7. A method of using the device of claim 4 for examining an object with ultrasound energy comprising:

selecting a group of M adjacent transducers in the row, M being less than or equal to N;

applying first electrical signals to at least part of the group of transducers, the signal being applied to each of the transducers being multiplied by a respective one of a first set of amplitude weighting factors, to transmit a beam of ultrasound energy from the group to the object;

receiving ultrasound energy in the beam, which is reflected from the object, with said group of transducers to produce second electrical signals;

applying the second signals to receive networks which multiply each of the second signals by a respective one of a second set of amplitude weighting factors; and applying the second signals to receive networks which multiply each of the second signals by a respective one of a third set of amplitude weighting factors;

wherein the second and third sets of weighting factors are different from each other and the sum of the weighting factors in the second set equals the sum of the weighting factors in the third set.

8. A device for examining an object with ultrasound energy comprising:

a row of N electroacoustic transducers which function to convert electrical transmission signals applied thereto into a beam of ultrasound energy which is directed toward the object and to convert ultrasound energy in the beam which is reflected by and received from the object into electrical receive signals;

an ultrasound transmitter for producing electrical transmission signals;

an ultrasound receiver for displaying electrical receive signals;

transmission network means for multiplying transmission signals produced by the ultrasound transmitter by a first set of amplitude weighting factors and by a fourth set of amplitude weighting factors;

receive network means for multiplying the receive signals by a second set of amplitude weighting factors and for applying the set of multiplied receive signals to the ultrasound receiver; and switching means for selectively connecting a group of M transducers in the row, M being less than or equal to N, to the transmission network means and to said receive network means so that a transmission signal multiplied by an associated one of the weighting factors in the first set is initially applied to each of the transducers in the group, so that a transmission signal multiplied by an associated one of the weighting factors in the fourth set is subsequently applied to each of the transducers in the group and so that the signals from each of the transducers in the group is multiplied by an associated one of the weighting factors in the second set of weighting factors;

wherein the first set of weighting factors and the fourth set of weighting factors are different from each other and wherein the sum of the weighting factors in the first set is equal to the sum of the weighting factors in the fourth set.

9. A method for using the device of claim 8 to examine an object with ultrasound energy comprising:

selecting a group of M adjacent transducers in the row, M being less than or equal to N;

initially applying first electrical signals to at least part of the group of transducers, the signals being applied to each of the transducers being multiplied by an associated one of a first set of amplitude weighting facts, to transmit a first beam of ultrasound energy to the object;

subsequently applying fourth electrical signals to at least a part of the group of transducers, the signals being applied to each of said transducers being multiplied by an associated one of a fourth set of amplitude weighting factors, to transmit a second beam of ultrasound energy to the object; and receiving ultrasound energy in the beams which is reflected from the object with the group of transducers to produce second electrical signals;

wherein the second and fourth set of weighting factors are different from each other and the sum of the weighting factors in the first set is equal to the sum of the weighting factors in the fourth set.

* * * * *